United States Patent

Hui

[11] Patent Number: 5,732,432
[45] Date of Patent: Mar. 31, 1998

[54] ELECTRIC TOOTHBRUSHES

[75] Inventor: Fung Kut Hui, Hong Kong, Hong Kong

[73] Assignee: Addway Engineering Limited, Hong Kong, Hong Kong

[21] Appl. No.: 753,099

[22] Filed: Nov. 20, 1996

[51] Int. Cl.⁶ .................................. A46B 13/02
[52] U.S. Cl. .................................. 15/22.1; 15/28
[58] Field of Search .................. 15/22.1, 23, 28

[56] References Cited

U.S. PATENT DOCUMENTS

| | | | |
|---|---|---|---|
| 1,692,980 | 11/1928 | Farmer | 15/23 |
| 2,379,049 | 6/1945 | Tompkins | 15/22.1 |
| 3,822,432 | 7/1974 | Skinner | 15/23 |
| 4,378,804 | 4/1983 | Cortese, Jr. | 15/23 |
| 5,054,149 | 10/1991 | Si-Hoe | 15/28 |
| 5,465,444 | 11/1995 | Bigler | 15/22.1 |

FOREIGN PATENT DOCUMENTS

| 0033753 | 3/1978 | Japan | 15/22.1 |
|---|---|---|---|

*Primary Examiner*—Randall Chin
*Attorney, Agent, or Firm*—Miller, Sisson, Chapman & Nash

[57] ABSTRACT

An electric toothbrush has an elongate shank and a drive shaft formed in two sections. The sections are drivingly coupled together by a coil spring. The shank is formed in two sections joined together by a flexible ribbed seal. The shank is able to flex while the drive shaft continues to run normally without adding strain to the electric motor which would increase electric power required. Rigid bars restrict the flexibility of the shank parts into a single plane.

4 Claims, 1 Drawing Sheet

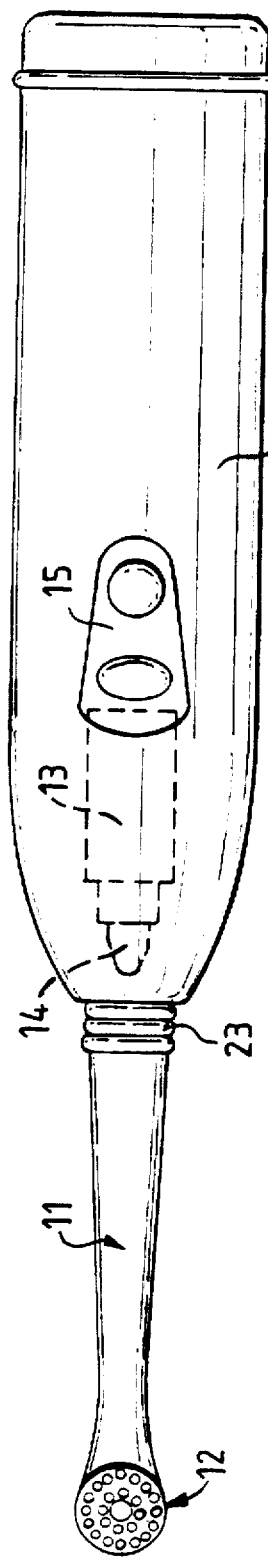
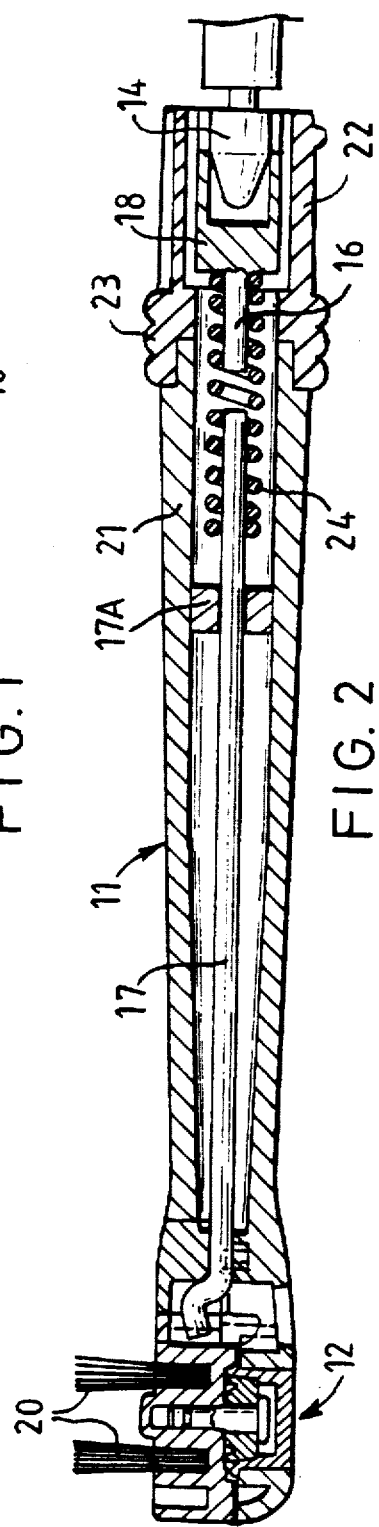
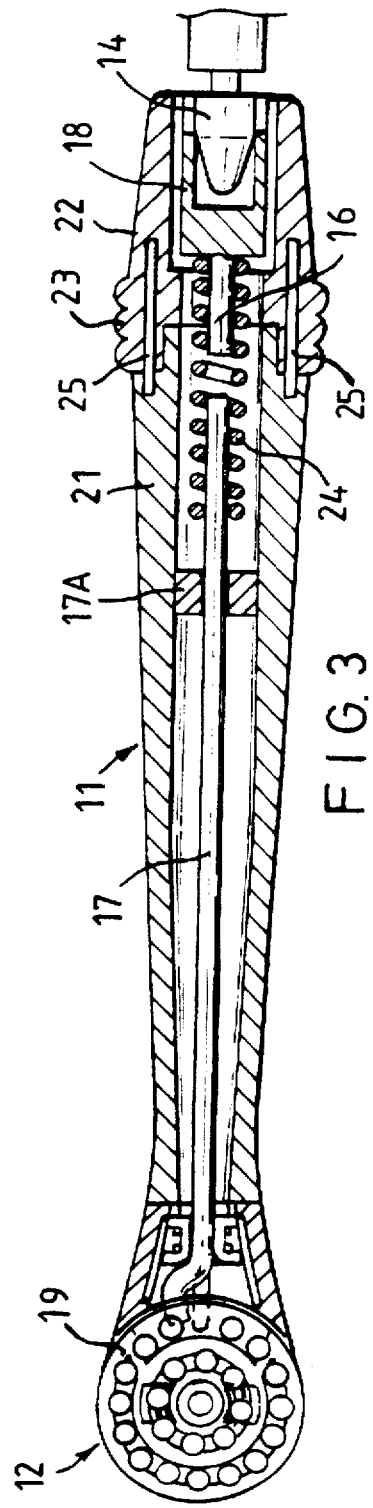

ELECTRIC TOOTHBRUSHES

BACKGROUND OF THE INVENTION

1. Field of the Invention

The invention relates to electric toothbrushes.

2. Description of Prior Art

The invention relates more particularly to battery operated electric toothbrushes. Such toothbrushes are generally light weight and comprise a handle containing a motor and a battery, and a brush head separated and joined to the handle by an elongate shank. A drive shaft extends from the motor to the head to rotate or vibrate bristles supported in the brush head as required and according to what the type of toothbrush is involved. Should the user apply significant pressure to his teeth, the shank may bend and strain the drive shaft and/or its mechanical connections at each end. Additionally, such bending of the shank and consequential mechanical misalignments can place considerable strain on the motor so that it draws more power and the effective battery life is reduced.

SUMMARY OF THE INVENTION

It is an object of the invention to overcome or at least reduce these problems.

According to the invention there is provided an electric toothbrush having a handle arranged to contain a motor, an elongate shank having one end mounted to the handle, a brush head mounted to the other end of the shank, and a drive shaft extending along inside the shank from the handle to the brush head, in which the shank is flexibly tiltable with respect to the handle and the drive shaft has a flexible drive coupling intermediate its length.

Bristles are mounted in the brush head with their axes extending at right angles to a central axis of the shank and the shank is preferably restrained to tilt relative to the handle in a plane generally parallel to the axes of the bristles.

The shank may have a first section at its one end that fits rigidly to the handle and a second section that fits rigidly to the brush head, and a flexible seal is provided to join and hold the first and second sections together.

The toothbrush may include opposing rigid bars extending between the first and second sections arranged to prevent the shank moving relatively to the handle in a plane at right angles to the axes of the bristles.

The flexible coupling is preferably positioned opposite the flexible seal.

The drive shaft may be in two separated aligned parts and the flexible coupling comprise a coiled spring that extends between and grips around opposing ends of the two parts.

BRIEF DESCRIPTION OF THE DRAWINGS

A toothbrush according to the invention will now be described by way of example with reference to the accompanying drawings in which:

FIG. 1 shows the toothbrush having a shank and a head;

FIG. 2 shows a cross-sectional side view of the shank and head in larger scale than FIG. 1 and FIG. 3 shows a cross-sectional bottom view of the shank and head also in the larger scale.

DESCRIPTION OF THE PREFERRED EMBODIMENT

Referring to the drawings, in FIG. 1 the toothbrush comprises a handle 10, an elongate shank 11 and a head 12.

The handle contains an electric motor 13 (shown dotted) and an output drive coupling 14 (shown dotted) and a battery (not shown). The handle has an ON-OFF switch 15 mounted on its outer surface.

In FIGS. 2 and 3, a drive shaft is formed in two somewhat separated sections 16 and 17. A bearing 17A is mounted inside the shank 11 to support the section 17. The section 16 has a cupped end 18 that receives the cone-shaped output coupling 14 of the motor 13 and extends a relatively short way along the overall length of the shank 11. The section 17 has one end next to an end of the section 16 and the other end mechanically coupled to a bristle mounting 19 rotatably supported in the head 12. A cranked remote end of the section 17 fits into a slot in the side of the head 19 so that rotation of the drive shaft causes the mounting 19 to rotate backwards and forwards about its central axis. Bristles 20, only two of which are shown in FIG. 2, are normally mounted in each of a plurality of holes in the head 19 with central axes of the bristles extending generally at right angles to a central longitudinal axis of the shank 11.

The shank 11 is also formed in two separate sections 21 and 22 joined together by a flexible ribbed seal 23. Generally opposite the seal 23 is the separation between the sections 16 and 17 of the drive shaft and a coil spring 24 fits over and grips the opposing ends of the sections 16 and 17 at either side of the separation. The spring is restrained at one end by a base of the cupped end 18. Normally there will be little or no tendency for the spring to move along the sections 16 and 17 but circlips or grooves formed in the periphery of the section 17 may be provided to locate an end or the ends of the spring 24 and restrain longitudinal movement thereof.

The seal 23 contains rigid opposing steel bars 25 that extend at their extreme ends into respective slots formed in the sections 21 and 22. The steel bars 25 prevent the distance between sections 21 and 22 shortening so that when viewed in FIG. 2 for example, the head 12 cannot move up or down because of the action of the bars 25. In other words, the head is constrained so as to move relative to the handle 10 only in a plane substantially parallel to the axes of the bristles 20. Such movement is permitted because the seal 23 is not otherwise restricted and can flex as appropriate. The mechanical coupling provided by the spring 24 is also sufficiently flexible to allow such respective tilting of the section 21 of the shank 11. Further, this tilting places very little, if any, extra mechanical strain on the drive shaft or its mechanical couplings at each end due to the flexibility of the coupling, provided by the spring, and so no extra electrical power is required by the motor 13.

The described toothbrush has a further possible advantage in practice. The user is normally inherently or visually aware of the flexing or tilting of the shaft and the degree of such relative movement of the head 12 during application of the bristles to his teeth and gums. A certain degree of tilt will appear to be acceptable because in normal general experiences, users know that all flexible devices usually have only a certain degree or limit of flexibility before permanent damage is likely. In the case of the described toothbrush, flexibility is controlled to an amount of tilting that is believed to be acceptable in mechanical terms to the user. This is well below the amount that would place too much pressure on the teeth, or more especially too much pressure on the gums. Thus, in practice the described toothbrush inherently incorporates user-regulated indications about the maximum pressure that can or should be applied during the cleaning of teeth.

The bars 25 may be omitted where desired so that the flexing of the shank can take place in any plane. Also, where the section 16 is somewhat longer, a bearing may be provided, similar to the bearing 17A, to support the remote end of the section 16 adjacent the spring 24, in a central position on a longitudinal axis of the handle 10.

We claim:

1. An electric toothbrush having a handle to contain a motor, an elongate shank having one end mounted to the handle, a brush head mounted to the other end of the shank, and a drive shaft extending along inside the shank from the handle to the brush head, in which the shank is flexibly tiltable with respect to the handle and the drive shaft has a flexible drive coupling intermediate its length, in which the shank has a first section at its one end that fits rigidly to the handle and a second section that fits rigidly to the brush head, and a flexible seal that joins and holds the first and second sections together.

2. A toothbrush according to claim 1, including opposing rigid bars extending between the first and second sections arranged to prevent the shank moving relatively to the handle in a plane at a right angle to the axes of the bristles.

3. A toothbrush according to claim 1, in which the flexible coupling is positioned opposite the flexible seal.

4. A toothbrush according to claim 1, in which the drive shaft is in two separated aligned parts and the flexible coupling comprises a coiled spring that extends between and grips around opposing ends of the two parts.

* * * * *